(12) United States Patent
O'Hern

(10) Patent No.: US 9,400,967 B2
(45) Date of Patent: Jul. 26, 2016

(54) DEVICES, SYSTEMS AND METHODS FOR PORTABLE DEVICE LOCATION

(75) Inventor: William A. O'Hern, Spring Lake, NJ (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 191 days.

(21) Appl. No.: 13/607,725

(22) Filed: Sep. 8, 2012

(65) Prior Publication Data

US 2012/0326930 A1    Dec. 27, 2012

Related U.S. Application Data

(63) Continuation of application No. 12/333,112, filed on Dec. 11, 2008, now Pat. No. 8,269,609.

(51) Int. Cl.
| | |
|---|---|
| *G01S 3/02* | (2006.01) |
| *G06Q 10/08* | (2012.01) |
| *H04W 64/00* | (2009.01) |
| *G01S 5/00* | (2006.01) |
| *H01M 10/42* | (2006.01) |
| *G06K 17/00* | (2006.01) |

(52) U.S. Cl.
CPC ............ *G06Q 10/087* (2013.01); *G01S 5/0063* (2013.01); *H01M 10/425* (2013.01); *H04W 64/00* (2013.01); *A61M 2205/8237* (2013.01); *G06K 2017/0045* (2013.01)

(58) Field of Classification Search
USPC .............. 701/117; 340/8.1, 572.1, 10.1, 10.2, 340/572.7; 250/370.09; 382/124; 235/492, 235/379, 499, 375, 380; 320/107; 710/117; 455/41.2, 551; 342/129
See application file for complete search history.

(56) References Cited

U.S. PATENT DOCUMENTS

| | | | |
|---|---|---|---|
| 5,528,222 A * | 6/1996 | Moskowitz et al. | 340/572.7 |
| 5,839,051 A * | 11/1998 | Grimmett et al. | 455/551 |
| 6,456,039 B1 | 9/2002 | Lauper et al. | |
| 6,854,657 B2 | 2/2005 | Johnson | |
| 6,892,052 B2 * | 5/2005 | Kotola et al. | 455/41.2 |
| 7,119,738 B2 * | 10/2006 | Bridgelall et al. | 342/129 |
| 7,382,904 B2 | 6/2008 | Lee | |
| 7,592,600 B2 | 9/2009 | Maschke | |
| 7,592,917 B2 * | 9/2009 | Quan et al. | 340/572.1 |
| 7,635,083 B2 | 12/2009 | Fukuda et al. | |
| 7,737,861 B2 * | 6/2010 | Lea et al. | 340/8.1 |

(Continued)

OTHER PUBLICATIONS

U.S. Office Action dated Dec. 7, 2011 in U.S. Appl. No. 12/333,112.

(Continued)

*Primary Examiner* — Omeed Alizada
(74) *Attorney, Agent, or Firm* — Hartman & Citrin LLC

(57) ABSTRACT

Devices, systems, and methods are disclosed which relate to a network of RFID readers which detect a location of an RFID transmitter coupled to a portable device. The network of RFID readers transmits the location to a user. The RFID transmitter couples to any personal device and broadcasts a unique ID. The nearest RFID reader(s) receive the unique ID and alert a server in communication with the network of RFID readers. The server calculates the distance of the RFID transmitter from each RFID reader receiving the unique ID. The server triangulates the location of the RFID transmitter when three or more RFID readers are receiving the unique ID. The server then securely transmits the location of the RFID transmitter to the user of the portable device. The user receives the transmission through a secure receiver.

15 Claims, 6 Drawing Sheets

(56) References Cited

U.S. PATENT DOCUMENTS

| | | | | |
|---|---|---|---|---|
| 8,036,820 | B2 * | 10/2011 | Sera | 701/117 |
| 8,376,216 | B2 * | 2/2013 | Morita | 235/375 |
| 2005/0116050 | A1 * | 6/2005 | Jei et al. | 235/492 |
| 2006/0076401 | A1 * | 4/2006 | Frerking | 235/380 |
| 2006/0175418 | A1 * | 8/2006 | Ho | 235/492 |
| 2007/0139162 | A1 * | 6/2007 | Bandy et al. | 340/10.2 |
| 2007/0273522 | A1 * | 11/2007 | Dembo et al. | 340/572.1 |
| 2008/0272889 | A1 * | 11/2008 | Symons | 340/10.1 |

OTHER PUBLICATIONS

U.S. Notice of Allowance dated May 11, 2012 in U.S. Appl. No. 12/333,112.

* cited by examiner

DEVICES, SYSTEMS AND METHODS FOR PORTABLE DEVICE LOCATION

This application is a continuation of U.S. patent application Ser. No. 12/333,112, filed Dec. 11, 2008, now U.S. Pat. No. 8,269,609, the content of which is hereby incorporated by reference herein in its entirety into this disclosure.

BACKGROUND OF THE INVENTION

1. Field of the Invention

The present invention relates to location of portable devices. More specifically, the present invention relates to wireless location of portable devices.

2. Background of the Invention

Today there are many portable electronic devices used by many on a daily basis. These devices are used extensively throughout the day and have become a dependency for many. Cellular telephones let users make calls from almost anywhere, allowing them to stay in constant contact. Personal digital assistants (PDAs) allow users to check e-mail and surf the internet away from the home or office. Portable music players let users listen to music on the go.

As technology progresses, these electronic devices are getting smaller and smaller. Devices once large now fit in the palm of one's hand. However, as the products get smaller, they also become easier to misplace. Frequently, a user is forced to attempt to call one's own cellular telephone to find its location. However, this does no good if the user does not even know where to begin to look, and depends on the cellular telephone having battery life remaining.

In addition to adults, kids are also using portable devices more and more. Kids all want some kind of mobile device to carry around with them, whether it's an IPOD, cellular telephone, digital camera, or any other type of mobile device. As typical with teenagers and kids, they leave them everywhere. Kids often leave devices somewhere and lose them. Half of the time they are not sure where the device is, where they left it, or what pocket it was in.

These devices are expensive, often costing hundreds of dollars. As technology has advanced, one device now performs the functions of what used to be six different devices. Many cellular telephones are now also cameras, and can be music players, PDAs, Global Positioning System (GPS) navigators, remote controllers, and portable video game systems. By losing one device a user loses the functionality of six devices.

With the size of devices, losing a device is a problem, but the theft of devices has also become much easier. A thief can pick up a small device and conceal it very easily, taking it away forever.

An RFID transmitter is an object that can be applied to objects for the purpose of identification and tracking. These transmitters are generally very small and lightweight, allowing them to be attached to objects for many different purposes. RFID transmitters send and receive radio-frequency (RF) signals to and from a reader. RFID transmitters generally contain two parts: an integrated circuit for signal modulation and storing and processing information, and an antenna for receiving and transmitting signals. RFID transmitters can be passive, active, or semi-passive. With passive RFID, the reader sends out a radio-frequency which provides enough power to the RFID transmitter for it to power up and transmit a response. Because the majority of RFID transmitters are passive and do not have a battery to power transmission, most RFID transmitters have a fairly short range. However, some transmitters can be read from several meters away and beyond the line of sight of the reader. Active RFID transmitters have an internal power source. This power source provides power to the integrated circuits to produce a powered transmission. This allows for a clearer transmitted signal with a longer range. Semi-passive RFID transmitters have their own power source, but only for powering the integrated circuit. The transmission of a signal is not powered by the power source.

Each RFID transmitter has a unique ID embedded in the signal it sends to a reader. RFID transmitters have been used in warehouses to keep track of an entire inventory for multiple stores down to every last individual product. Even a single pack of bubble gum has its own unique RFID transmitter.

What is needed is a system that allows tracking of these ever-shrinking portable devices no matter where you lose them. The system should identify every device uniquely so that, once found, a user can be absolutely certain a device is their property.

SUMMARY OF THE INVENTION

The present invention features a network of RFID readers which detect a location of an RFID transmitter coupled to a portable device. The network of RFID readers transmits the location to a user. The RFID transmitter couples to any personal device and broadcasts a unique ID. The nearest RFID reader(s) receive the unique ID and alert a server in communication with the network of RFID readers. The server calculates the distance of the RFID transmitter from each RFID reader receiving the unique ID. The server triangulates the location of the RFID transmitter when three or more RFID readers are receiving the unique ID. The server then securely transmits the location of the RFID transmitter to the user of the portable device.

Furthermore, the user can receive the location in many different forms. The user may logon to a web portal to receive the location of the portable device on a map upon request. The user may also download the longitude and latitude to a GPS navigator. The user may even be alerted of the location automatically on a periodic or non-periodic basis. This alert can be sent as an email, a Short Message Service (SMS) text message, a voice mail, etc.

In one exemplary embodiment, the present invention is a portable device tracking system comprising an RFID transmitter coupled to a portable device, a plurality of RFID readers, which can detect an RFID transmitter, distributed about an area, a server in communication with the plurality of RFID readers, and a secure receiver in communication with the server. The server calculates a location based on one or more readings from the plurality of RFID readers and transmits the location securely to a user through the secure receiver.

In another exemplary embodiment, the present invention is a portable electronic device comprising a battery, two exposed device electrical contacts, and a removable active RFID transmitter having two exposed transmitter electrical contacts coupled with the portable electronic device. The RFID transmitter is oriented such that the device electrical contacts touch the transmitter electrical contacts allowing the battery to power the removable active RFID transmitter.

In a further exemplary embodiment, the present invention is a portable device tracking system comprising an RFID transmitter coupled to a personal device, a plurality of RFID readers which detect the RFID transmitter, a server in communication with the plurality of RFID readers, a logic on the server which calculates a distance of the RFID transmitter read by an RFID reader, and a secure receiver in communication with the server. A user locates the personal device by receiving a location of the personal device calculated by the logic anywhere the personal device is detectable by at least one RFID reader.

In yet another exemplary embodiment, the present invention is a method of tracking a portable device comprising reading an RFID transmitter with one or more RFID readers, calculating a distance of the RFID transmitter from each of the RFID readers, and outputting a location of the RFID transmitter. A user securely receives the location of the RFID transmitter.

DETAILED DESCRIPTION OF THE INVENTION

The present invention features a network of RFID readers which detect a location of an RFID transmitter coupled to a portable device. The network of RFID readers transmits the location to a user. The RFID transmitter couples to any personal device and broadcasts a unique ID. The nearest RFID reader(s) receive the unique ID and alert a server in communication with the network of RFID readers. The server calculates the distance of the RFID transmitter from each RFID reader receiving the unique ID. The server triangulates the location of the RFID transmitter when three or more RFID readers are receiving the unique ID. The server then securely transmits the location of the RFID transmitter to the user of the portable device. The user receives the transmission through a secure receiver.

"Location," as used herein and throughout this disclosure, refers to an inexact position. An RFID reader reads an inexact distance of an RFID transmitter, but the accuracy can be improved by a system which reads the distance from more RFID readers. Initially, the first reader can only determine a perimeter in which the RFID transmitter lies, absent a direction. However, as each new RFID reader reads an RFID transmitter, the location becomes more and more exact. Thus, the accuracy of a "location" will change with the number of RFID readers that read an RFID transmitter.

FIGS. 1A-1D show various embodiments of RFID transmitters used in the present invention. RFID transmitters may be active, passive, or semi-passive, depending on the signal strength necessary for the system in place. RFID transmitters may be attached to a device, such as with an adhesive, inserted into a port in a device, etc.

Figure 1A:
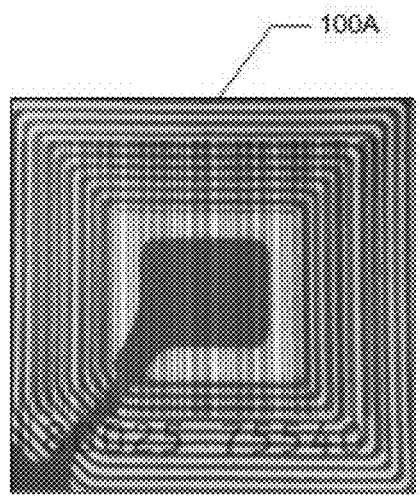
FIG. 1A shows a passive RFID transmitter, according to an exemplary embodiment of the present invention.

FIG. 1A shows a passive RFID transmitter 100A, according to an exemplary embodiment of the present invention. In this embodiment, passive RFID transmitter 100A does not have a power source. The integrated circuit in RFID transmitter 100A is powered by signals from a reader. When a signal is received from a reader, the integrated circuit powers up and transmits its unique ID. RFID transmitter 100A may be small and thin, such that it can be attached with adhesive to a device without adding bulk or changing the dimensions of the device.

Figure 1B:
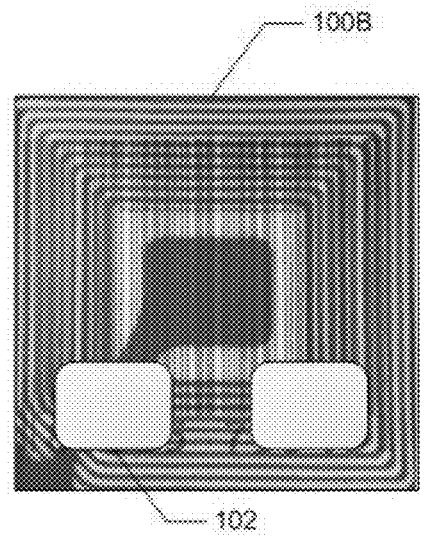
FIG. 1B shows an active RFID transmitter, according to an exemplary embodiment of the present invention.

FIG. 1B shows an active RFID transmitter 100B, according to an exemplary embodiment of the present invention. In this embodiment, RFID transmitter 100B includes at least two contacts 102 used to connect RFID transmitter 100B with a power source, such as a battery. The power source provides power to the integrated circuit and generally assists RFID transmitter 100B to transmit a further distance than a passive RFID transmitter. RFID transmitter 100B may be small and thin, such that it can be attached to a portable electronic device in concealed areas. For example, RFID transmitter 100B may be attached underneath the battery of a cellular telephone such that it is completely hidden from the outside. Most battery powered electronic devices such as cellular telephones and digital media players require much more battery power than an RFID transmitter. In most cases, when the battery no longer has enough power to run the electronic device itself, it still has enough power to run the RFID transmitter. Thus, the RFID transmitter remains active even though the device is off.

Figure 1C:
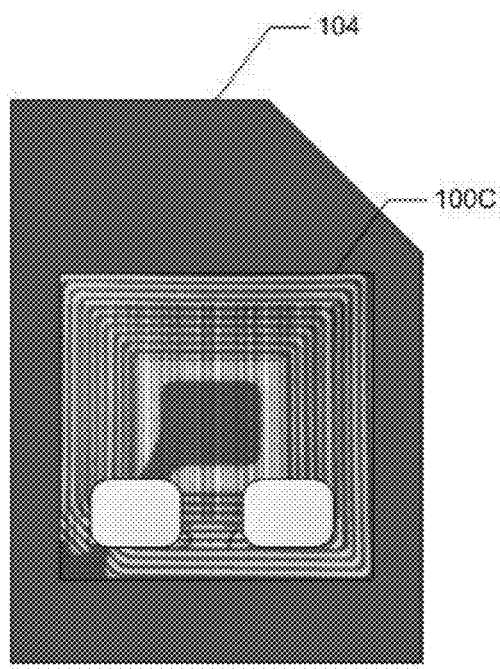
FIG. 1C shows an active RFID transmitter, according to an exemplary embodiment of the present invention.

FIG. 1C shows an active RFID transmitter 100C, according to an exemplary embodiment of the present invention. In this embodiment, RFID transmitter 100C is attached to a card 104 and can be inserted into a port on a portable electronic device. RFID transmitter 100C contains at least two contacts to connect RFID transmitter 100C with the power source of the portable electronic device, such as a battery. The power source provides power to the integrated circuit of RFID transmitter 100C. The power source also assists RFID transmitter 100C to transmit. In embodiments of the present invention, RFID transmitter 100C additionally transmits using the portable electronic device's antenna. This embodiment of the RFID transmitter is also capable of remaining active even though the device is off.

Figure 1D:
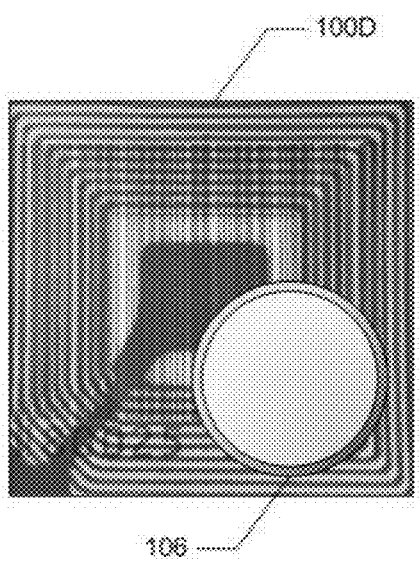
FIG. 1D shows an active RFID transmitter, according to an exemplary embodiment of the present invention.

FIG. 1D shows an active RFID transmitter 100D, according to an exemplary embodiment of the present invention. In this embodiment, RFID transmitter 100D contains an onboard power source 106, such as a watch battery. Onboard power source 106 provides power to the integrated circuit of RFID transmitter 100D. Onboard power source 106 also assists RFID transmitter 100D in transmitting the unique ID.

Figure 2:
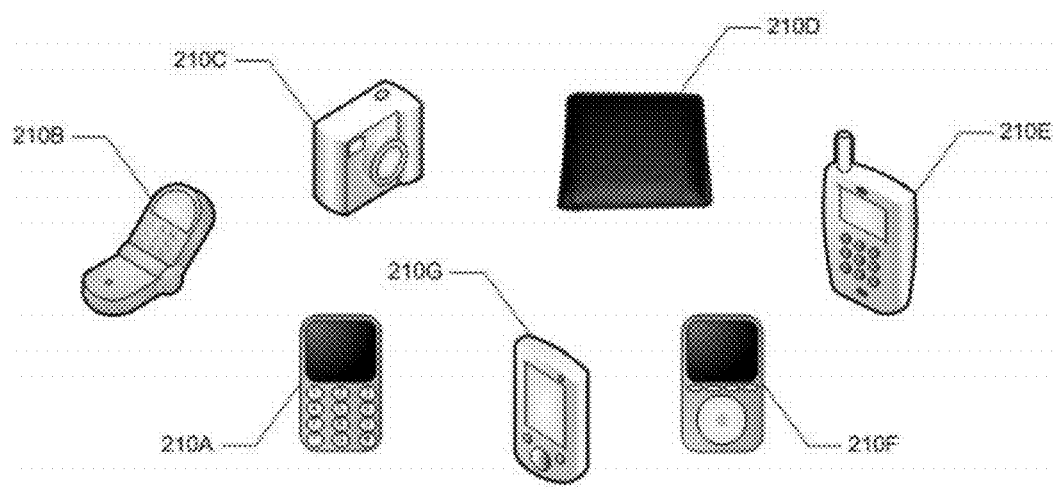
FIG. 2 shows various portable devices utilizing RFID transmitters, according to an exemplary embodiment of the present invention.

FIG. 2 shows various portable devices utilizing RFID transmitters, according to an exemplary embodiment of the present invention. In this embodiment, devices include smart phone 210A, flip phone 210B, camera 210C, wallet 210D, cellular telephone 210E, digital media player 210F, and PDA 210G. Many of these devices may use any of the types of RFID transmitters, including an active RFID transmitter with electric contacts. Other non-electronic devices, such as wallet 210D, use either a passive RFID transmitter or an active RFID transmitter with an onboard power supply. RFID transmitters may be discretely placed on each device. These RFID transmitters allow the device to be located by a system in the event they are lost or stolen. The RFID transmitters can be attached with adhesive to the device, inserted into a port on the device, placed inside the device, etc.

Figures 3A, 3B:
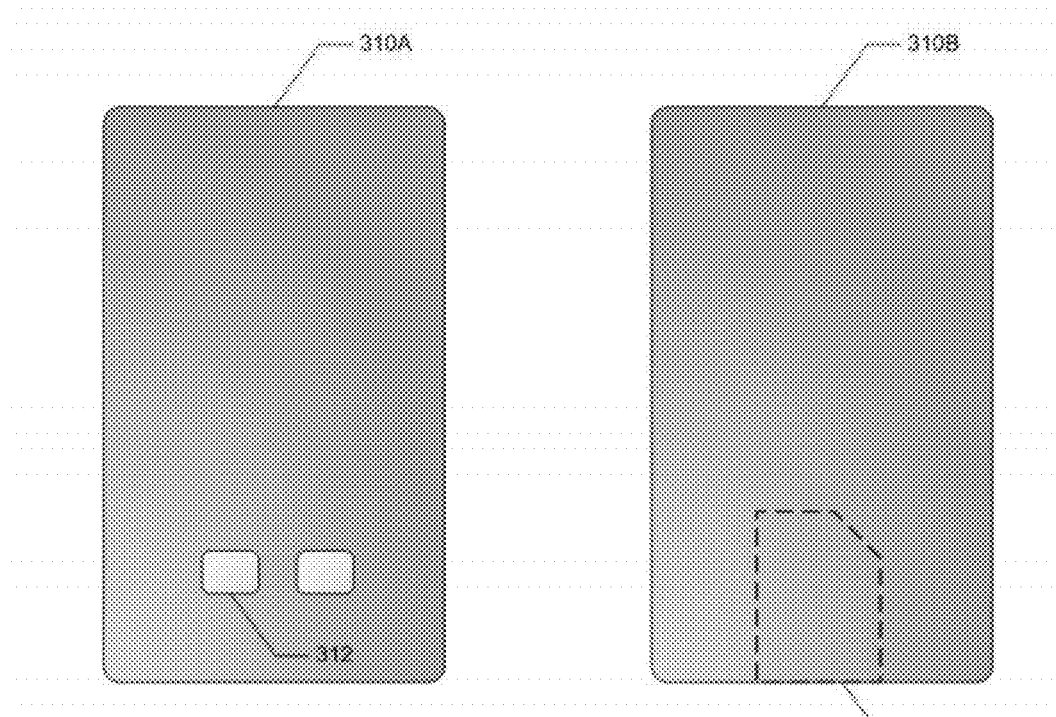
FIG. 3A shows a portable electronic device for use with an RFID transmitter, according to an exemplary embodiment of the present invention.
FIG. 3B shows a portable electronic device for use with an RFID transmitter, according to an exemplary embodiment of the present invention.

FIG. 3A-3B show portable devices with special placement areas, according to an exemplary embodiment of the present invention. These placement areas integrate the RFID transmitter into the device, either for concealment, or to provide a power source to the RFID transmitter.

FIG. 3A shows a portable electronic device 310A for use with an RFID transmitter, according to an exemplary embodiment of the present invention. In this embodiment, electronic device 310A has contacts 312 which allow an active RFID transmitter to attach to the power source of electronic device 310A. The RFID transmitter may be attached to electronic device 310A using adhesive, with the contacts of the RFID transmitter coupled to contacts 312. One of the contacts 312 is the positive terminal while the other is the negative terminal. Since the RFID transmitter can only operate with current running in one direction, it is important to match the positive contact with the correct RFID contact. Reversing the contacts may result in an inoperable and possibly damaged RFID transmitter.

FIG. 3B shows a portable electronic device 310B for use with an RFID transmitter, according to an exemplary embodiment of the present invention. In this embodiment, electronic device 310B has a slot 314 for receiving the RFID transmitter. Slot 314 may receive a passive RFID transmitter, wherein the RFID transmitter is not connected to a power supply, an active or semi-passive RFID transmitter with an attached power supply, or an active or semi-passive RFID transmitter with contacts, wherein the slot provides a connection to a power supply within electronic device 310B. The shape of the slot and the RFID transmitter prevents accidental reversal of the contacts as is possible with the embodiment in FIG. 3A.

Figure 4:
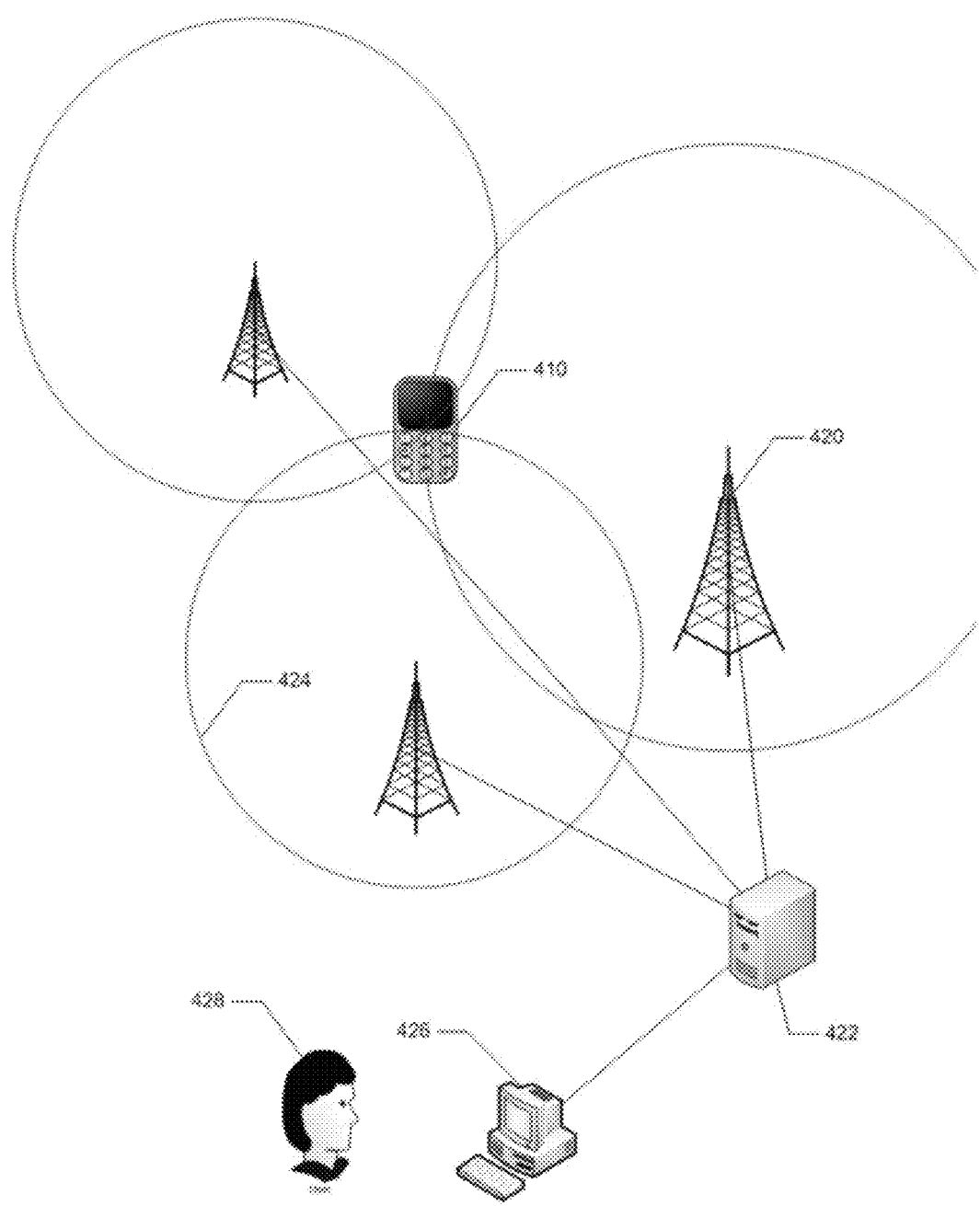
FIG. 4 shows a system for locating a device coupled with an RFID transmitter, according to an exemplary embodiment of the present invention.

FIG. 4 shows a system for locating a device 410 coupled with an RFID transmitter, according to an exemplary embodiment of the present invention. In this embodiment, the system comprises a computer 426, a server 422, an RFID reader 420, and a read distance 424. When a user 428 has lost a portable device 410, user 428 logs into server 422 using computer 426. Logging in may include entering a user name, password, device number, etc. Server 422 is in contact with multiple RFID readers. RFID reader 420 sends out a signal. When the RFID transmitter on portable device 410 receives the signal, the integrated circuit of the RFID transmitter powers up and then transmits a signal back containing a unique ID. RFID reader 420 receives the signal from the RFID transmitter and determines the identity and distance of the RFID transmitter. The distance is determined by measuring the time it takes for the RFID transmitter to respond. The longer the reader 420 waits to receive a response the farther away the RFID transmitter must be. Identity of the device 410 is important for users who have more than one device input in the system, and because more than one user may have devices in the system. The first RFID reader 420 to receive a response from the RFID transmitter can only give a read distance 424, yielding a perimeter of possible locations of the portable device 410. However, multiple RFID readers allow the system to determine an approximate location of portable device 410. In exemplary embodiments of the present invention, this determination is accomplished by triangulating the location from three different RFID readers 420. Using three or more RFID readers 420 provides a more precise location. Once the approximate location of portable device 410 is determined, server 422 notifies user 428 of this location. The notification occurs through a receiver, such as computer 426 connected to a web portal. In other exemplary embodiments the receiver is a GPS navigator, another portable device, etc. The notification is in the form of a map with a location marked, such as with GOOGLE MAPS, MAPQUEST, etc. In other exemplary embodiments of the present invention, the location is marked with a light which blinks if the device is moving. The notification can also be in the form of an e-mail, a Short Message Service (SMS) text message, a voice mail, etc.

Depending upon the strength of the RFID transmitters and RFID readers 420, the RFID readers 420 can be located in many nearby locations, similar to WIFI hotspots, or far away, such as RFID readers attached to cellular towers. RFID readers 420 may be purchased for a home such that portable devices in the home can be easily located.

Figure 5:
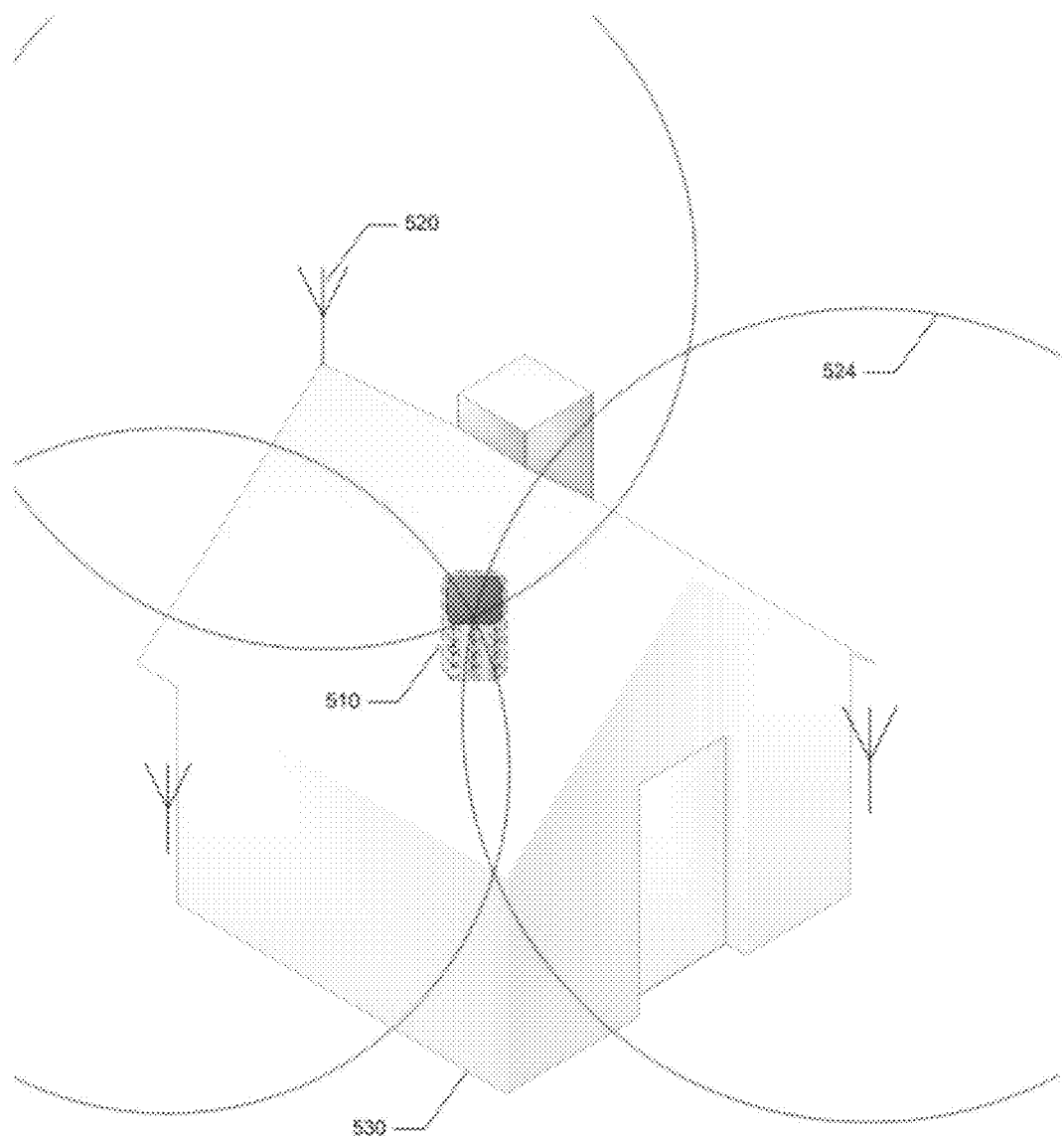
FIG. 5 shows multiple RFID readers in a home environment, according to an exemplary embodiment of the present invention.

FIG. 5 shows multiple RFID readers in a home environment 530, according to an exemplary embodiment of the present invention. In this embodiment, multiple RFID readers 520 are placed around home 530. Depending upon the strength of the signals generated, the RFID readers 520 can be placed at the corners of the house, at the corners of a room, around a desk, etc. Each reader 520 broadcasts a signal to detect RFID transmitters, such as the RFID transmitter on device 510. The signal is received by the RFID transmitters within range, causing the integrated circuit of each RFID transmitter to power up. For passive RFID, the signal itself powers up the integrated circuit. With active RFID transmitters, a power source powers up the integrated circuit. The RFID transmitter then transmits a signal, with active RFID using a power source to transmit, which is received by RFID readers 520. Each reader 520 has a read distance 524, which is a distance from the reader 520 at which device 510 is located. In order to determine read distance 524, each RFID reader 520 must know the response time. The RFID reader 520 must know to which broadcast the RFID transmitter is responding. If all the RFID readers 520 are broadcasting at the same time in succession, then this is difficult to determine. Each RFID reader 520 must produce its own broadcast and wait for a response. After each RFID reader 520 has taken its turn, the location can be triangulated. By using multiple RFID readers 520, the read distances from each reader 520 are matched such that a location of device 510 is determined. With three or more readers 520, the location of device 510 is triangulated, such that a precise location is determined. This embodiment is not limited to a house. It is just as easily utilized in an office, store, park, school, etc.

In other exemplary embodiments, third parties may have these RFID systems and detectors to keep track of their inventory. These third parties, such as stores, malls, warehouses, etc., may additionally track mobile devices that have RFID transmitters. When a device with an RFID transmitter enters or leaves their premises that unique ID is submitted a database in case someone is looking for their lost or stolen device. Though the device may travel out of the range of an RFID reader in the future, the user will know it was in or near a particular store at a certain time.

Figure 6:
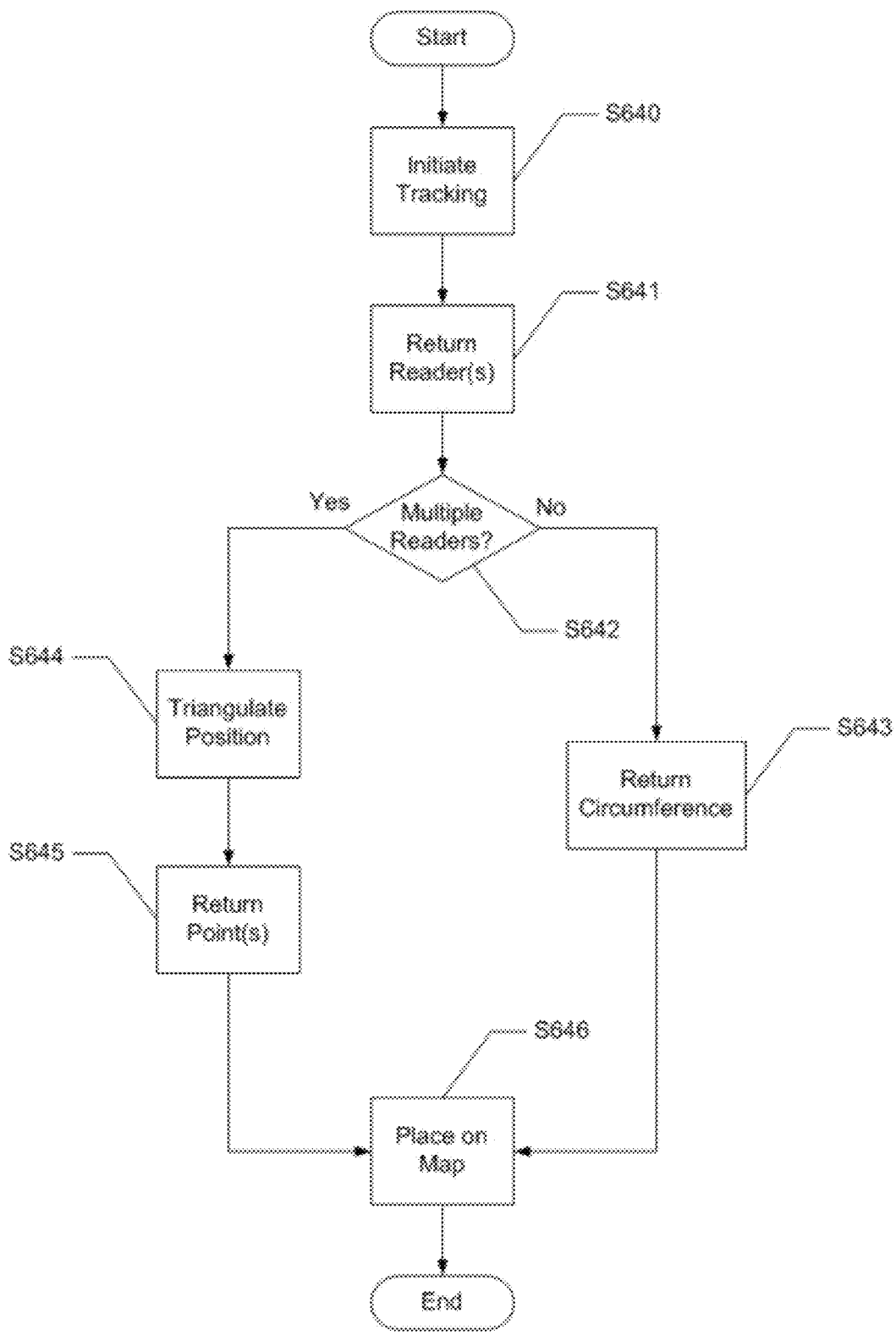
FIG. 6 shows a flowchart of a method for locating a device, according to an exemplary embodiment of the present invention.

FIG. 6 shows a flowchart of a method for locating a device, according to an exemplary embodiment of the present invention. In this embodiment, the device has an attached RFID transmitter, the ID and information of which is already in the system. A user logs into the system's server through a computer or other device to initiate tracking of a lost or stolen portable device S640. Each RFID reader in the system searches an area by broadcasting a signal. This signal causes a response from an RFID transmitter if any RFID transmitter is present. Any RFID reader which detects a response sends the distance of the signal origin to the server S641. The system queries whether there are multiple readers detecting a signal from the same RFID transmitter S642. If there are not multiple readers, the system determines a circumference around the reader detecting the RFID transmitter signal S643. This is because RFID reader detects a distance, not a direction. If multiple readers each detect the same RFID transmitter, the position of the RFID transmitter is triangulated S644. This is accomplished by overlaying the circumference of the distance detected by each of the readers. The triangulation returns a point or points where the device should be located S645. With the detection by only two RFID readers, the location may be narrowed down to two points. With three or more RFID readers, the position may be narrowed to one point. The point or points determined by the system are placed on a map S646. This location on a map is returned to the user so that the user can search that location for the device.

Figure 7:
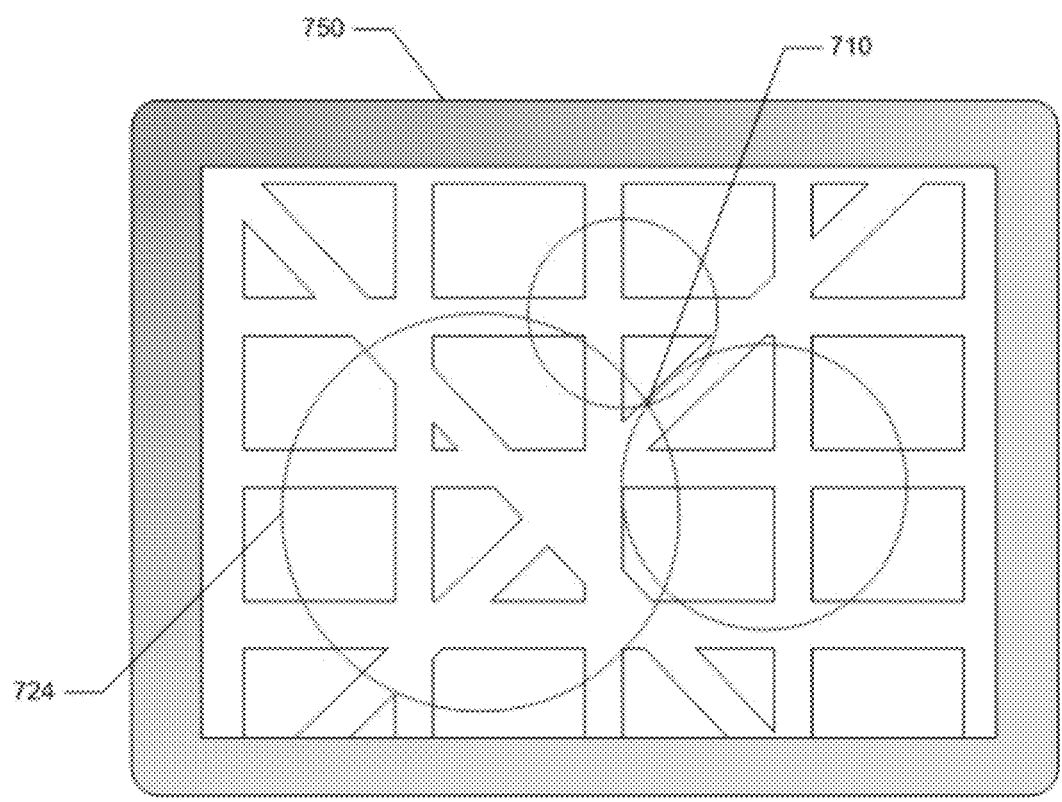
FIG. 7 shows a map of the location of a portable device, according to an exemplary embodiment of the present invention.

FIG. 7 shows a map of the location of a portable device, according to an exemplary embodiment of the present invention. In this embodiment, a location output 750 to a user is a map with the triangulation of a device 710. The circumference composed of a read distance 724 from each RFID reader is shown. At the intersection of the read distances 724 is the location of device 710. A user may go to this location to find device 710. In alternative embodiments, simply the location itself is sent to user. Exemplary embodiments of the invention send this map through a web portal to any computer.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A portable device tracking server comprising:
a processor; and
a memory that stores instructions that, when executed by the processor, cause the processor to perform operations comprising
receiving, from a computer, a request to locate a portable device comprising a radiofrequency identification transmitter;
receiving, from three radiofrequency identification readers, three distances, wherein each of the three radiofrequency identification readers calculates a one of the three distances by
broadcasting a broadcast signal to an area,
receiving, from the radiofrequency identification transmitter located in the area a response signal, and
calculating the one of the three distances by measuring a time for the radiofrequency identification transmitter to respond to the broadcast signal;
determining, based upon the three distances calculated, a location of the portable device, wherein the location is determined using triangulation;
transmitting the location determined to the computer via a secure receiver, wherein each of the three radiofrequency readers broadcasts the broadcast signal and waits for a response from the radiofrequency identification transmitter before a next of the three radiofrequency identification readers broadcasts the broadcast signal, wherein the portable device comprises a battery and a pair of exposed device electrical contacts configured to mate with a corresponding pair of exposed transmitter electrical contacts of the radiofrequency identification transmitter to power the radiofrequency identification transmitter via the battery.

2. A method, comprising:
receiving, at a server comprising a processor and from a computer, a request to locate a portable device comprising a radiofrequency identification transmitter;
receiving, at the server and from three radiofrequency identification readers, three distances, wherein each of the three radiofrequency identification readers calculates a one of the three distances by
broadcasting a broadcast signal to an area,
receiving, from the radiofrequency identification transmitter located in the area a response signal, and
calculating the one of the three distances by measuring a time for the radiofrequency identification transmitter to respond to the broadcast signal;
determining, by the server and based upon the three distances calculated, a location of the portable device, wherein the location is determined using triangulation;
transmitting, by the server and to the computer via a secure receiver, the location determined, wherein each of the three radiofrequency readers broadcasts the broadcast signal and waits for a response from the radiofrequency identification transmitter before a next of the three radio frequency identification readers broadcasts the broadcast signal, wherein the portable device comprises a battery and a pair of exposed device electrical contacts configured to mate with a corresponding pair of exposed transmitter electrical contacts of the radiofrequency identification transmitter to power the radiofrequency identification transmitter via the battery.

3. The portable device tracking server of claim 1, wherein the portable device comprises a mobile telephone.

4. The portable device tracking server of claim 1, wherein the computer displays the location of the portable device on a map.

5. The portable device tracking server of claim 1, wherein the location is provided to the computer as a short messaging service message.

6. The portable device tracking server of claim 1, wherein the three radiofrequency identification readers are distributed about the area.

7. The method of claim 2, wherein the portable device comprises a mobile telephone.

8. The method of claim 2, wherein the computer displays the location of the portable device on a map.

9. The method of claim 2, wherein the location is provided to the computer as a short messaging service message.

10. The method of claim 2, wherein the three radiofrequency identification readers are distributed about the area.

11. A system comprising: a processor; and
a memory that stores instructions that, when executed by the processor, cause the processor to perform operations comprising
receiving, from a computer, a request to locate a portable device comprising a radiofrequency identification transmitter;
receiving three distances from three radiofrequency identification readers, wherein each of the three radiofrequency identification readers calculates a one of the three distances by
broadcasting a broadcast signal to an area,
receiving, from the radiofrequency identification transmitter located in the area a response signal, and
calculating the one of the three distances by measuring a time for the radiofrequency identification transmitter to respond to the broadcast signal; determining, based upon the three distances calculated, a location of the portable device, wherein the location is determined using triangulation;
transmitting the location determined to the computer via a secure receiver, wherein each of the three radiofrequency readers broadcasts the broadcast signal and waits for a response from the radiofrequency identification transmitter before a next of the three radiofrequency identification readers broadcasts the broadcast signal, wherein the portable device comprises a battery and a pair of exposed device electrical contacts configured to mate with a corresponding pair of exposed transmitter electrical contacts of the radiofrequency identification transmitter to power the radiofrequency identification transmitter via the battery.

12. The system of claim 11, wherein the portable device comprises a mobile telephone.

13. The system of claim 11, wherein the computer displays the location of the portable device on a map.

14. The system of claim 11, wherein the location is provided to the computer as a short messaging service message.

15. The system of claim 11, wherein the three radiofrequency identification readers are distributed about the area.

* * * * *